United States Patent [19]

Miller

[11] 4,275,905
[45] Jun. 30, 1981

[54] PRESSURE-SENSITIVE RECORD MATERIAL

[75] Inventor: Robert E. Miller, Appleton, Wis.

[73] Assignee: Appleton Papers Inc., Appleton, Wis.

[21] Appl. No.: 45,769

[22] Filed: Jun. 5, 1979

Related U.S. Application Data

[63] Continuation-in-part of Ser. No. 375, Dec. 29, 1978, abandoned.

[51] Int. Cl.³ .................... B41M 5/16; B41M 5/22; C09D 11/00
[52] U.S. Cl. .................... 282/27.5; 106/14.5; 106/21; 252/316; 427/151; 428/307; 428/914
[58] Field of Search .............. 106/21, 14.5, 22, 27, 106/28, 32; 282/27.5; 427/150, 151; 428/307, 914, 411, 537, 913; 252/316

[56] References Cited

U.S. PATENT DOCUMENTS

| | | |
|---|---|---|
| 3,775,424 | 11/1973 | Farber .................................. 546/116 |
| 3,853,869 | 11/1974 | Farber .............................. 546/116 X |
| 4,012,554 | 3/1977 | Miller et al. ...................... 428/307 X |

Primary Examiner—Bruce H. H. Hess
Attorney, Agent, or Firm—Birch, Stewart, Kolasch and Birch

[57] ABSTRACT

A substantially colorless marking liquid, particularly for use in pressure-sensitive record material, comprising (a) a colorless chromogenic material, (b) a solvent for said chromogenic material and (c) an additive for controlling CB decline. The additive for controlling CB decline, i.e., controlling the capability of the CB sheet to produce an image of satisfactory intensity even after exposure of the CB coating to light, includes certain chromogenic materials such as Pyridyl Blue and phenol derivatives having a free reactive (ortho- or para-) position. The marking liquid helps to prevent CB decline in, for example, carbonless copy paper, a long-standing problem in the art.

14 Claims, No Drawings

PRESSURE-SENSITIVE RECORD MATERIAL

This application is a Continuation-in-Part of copending application Ser. No. 375, filed on Dec. 29, 1978 now abandoned.

BACKGROUND OF THE INVENTION

This invention relates to a multi-component substantially colorless marking liquid for use in a pressure-sensitive record material. More particularly, the invention relates to a reactive marking liquid which produces distinctive marks on properly sensitized record material by absorbing some or substantially all of the visible spectrum of light between a wavelength of 400 to 700 millimicrons.

Pressure-sensitive record materials employing colorless chromogenic compounds which form a mark when contacted with an acidic substance are well known in the art. Exemplary thereof are Crystal Violet Lactone (CVL) as described in Reissue patent No. 23,024 and the systems disclosed in U.S. Pat. Nos. 3,509,173 (3,3-bis(1-ethyl-2-methylindol-3-yl)phthalide, also known as Indolyl Red) and 3,681,390 (2'-anilino-3'-methyl-6'-diethylaminofluoran, also known as N-102 dye).

Liquid organic solvent solutions of the colorless chromogenic compounds are normally encapsulated and coated on the back side (CB) of sheets contained in a manifold record system. An acidic clay or resin is then coated on the front side (CF) of these sheets. When such sheets are placed in contiguous relationship, the microscopic rupturable capsules of colorless chromogenic compound from a mark upon capsule rupture and transfer and reaction of the capsule contents with the acidic material when pressure is applied thereto. Alternatively, the capsules of dye precursor or colorless chromogenic compound and acidic material may be coated on the same side of the record sheets, whereby the rupture of the capsules upon the application of pressure permits the admixture of the dye precursor with the acidic material and consequent mark formation.

The liquid solvent portion of the mark-forming liquid can be volatile or non-volatile and can constitute a single or multiple component solvent which is wholly or partially volatile. Some of the solvent system used in the prior art provide adequate print speed and color intensity on the widely used phenolic resin receiving sheets. However, certain of these prior art solvents are also known to cause problems, such as unsatisfactory retention of the ability of the CB sheet to produce an image of acceptable intensity after exposure of the CB coating to light. This reduction in ability to produce a satisfactory image after accelerated light exposure is called CB decline.

The chromogenic system itself is also, of course, critical in obtaining a satisfactory pressure-sensitive record material. Specifically, the mark formation must be intense and resistant to fade or change in color as well as being resistant to CB decline. Many of the prior art chromogenic systems are, however, prone to said CB decline.

As noted above, CVL has been widely used in commercially available carbonless copy paper systems. More recently, however, for a variety of reasons, the industry has been seeking new and alternative dye systems. These include compounds related to the Pyridyl Blue dye compound disclosed in the present application. For example, U.S. Pat. Nos. 3,775,424 and 3,853,869 of Farber disclose certain pyridine and pyrazine compounds which are closely related to Pyridyl Blue. Likewise, Japanese Kokai No. 75-05116 (Chem. Abstracts, Vol. 83, 3579v, 1975), Japanese Kokai No. 75-03426 (Chem. Abstracts, Vol. 83, 29895v, 1975) and Japanese Kokai No. 74-118515 (Chem. Abstracts, Vol. 82, 178280x, 1974) teach similar systems. However, none of these references teaches or suggests the critical proportions of dyes, solvents and other materials necessary for achieving the objectives of the present invention.

For instance, 2,2,4-trimethyl-1,3-pentanediol diisobutyrate, also known as TXIB, is an odorless, active solvent with acceptable toxicological properties. However, unless a major portion of CVL is replaced with Pyridyl Blue in the chromogenic system, or other materials are added, unacceptable results for CB decline tests are observed. Thus, one way to use TXIB successfully as a carbonless paper solvent in this context is to change the color former. Accordingly, as is shown below in Example 30, a color former containing Pyridyl Blue demonstrates a remarkable resistance to CB decline in a TXIB solvent.

SUMMARY OF THE INVENTION

An object of the invention is to provide a colorless marking liquid for use in pressure-sensitive record material having excellent resistance to light exposure of the CB coating (CB decline).

Another object of the invention is to provide a colorless marking liquid for use in pressure-sensitive record material having excellent fade resistance and hue stability.

A further object of the present invention is to provide a colorless marking liquid which has little or no detectable odor.

These and other objects and advantages of the present invention will become apparent to those skilled in the art from a consideration of the following specification and claims.

In accordance with the present invention, it has been found that said objectives, and particularly the resistance to CB decline, can be attained by utilizing a colorless marking liquid composition comprising a chromogenic material, a solvent material and, in some cases, an additive specifically designed to control CB decline. Pyridyl Blue itself, if used as the color former, is capable of controlling CB decline to an acceptable level. Phenol derivatives having a free reactive position (i.e., the ortho- or para-position with respect to the hydroxy function on the phenol molecule) are acceptable additives for controlling CB decline. Either Pyridyl Blue or said phenol additive works well alone to control CB decline; a combination of Pyridyl Blue and a phenol produce excellent results.

DETAILED DESCRIPTION OF THE INVENTION

The colorless chromogenic compounds or reactants which can be used in the mark-forming liquids of the invention comprise one or more of the following compounds: Pyridyl Blue, which is an isomeric mixture of 7-(1-ethyl-2-methylindol-3-yl)-7-(4-diethylamino-2-ethoxyphenyl)-5,7-dihydrofuro[3,4-b]pyridin-5-one and 5-(1-ethyl-2-methylindol-3-yl)-5-(4-diethylamino-2-ethoxyphenyl)-5,7-dihydrofuro[3,4-b]pyridin-7-one; benzoyl leuco methylene blue (BLMB), which is 3,7-bis(dimethylamino)-10-benzoyl-phenothiazine; Crystal Violet Lactone (CVL), which is 3,3-bis(4-dimethylaminophenyl)-6-dimethylaminophthalide; N-102, which is 2'-anilino-6'-diethylamino-3'-methylfluoran; Indolyl Red, which is 3,3-bis(1-ethyl-2-methylindol-3-yl)phthalide; 3,3-bis(1-butyl-2-methylindol-3-yl)phthalide; spiro-7-chloro-2,6-dimethyl-3-ethylaminoxanthene-9,2-(2H)naphthol [1,8-bc]furan; 7-chloro-6-methyl-3-diethylaminofluoran; 3-diethylamino-benzo[b]fluoran; 3-(4-diethylamino-2-ethoxy)-3-(2-methyl-1-ethylindol-3-yl)phthalide; 3-(4-diethylamino-2-butoxy)-3-(2-methyl-1-ethylindol-3-yl)phthalide; and 3,7-bis(diethylamino)-10-benzoylbenzocazine. In a chromogenic system comprising Pyridyl Blue, the latter dyes can be employed as a toner for the Pyridyl Blue to give the desired hue or color tone.

The amount of Pyridyl Blue employed in the preferred mark-forming liquid of the invention ranges from about 0.6 to about 3 weight percent (based on parts by weight per 100 parts by weight of internal phase solvent). The amount of BLMB to be used therewith ranges from 0% up to about 1.3 weight percent. The amount of CVL ranges from 0% up to about 3 weight percent, the amount of Indolyl Red (IR) from 0% up to about 2 weight percent and the amount of N-102 dye from 0% up to about 3 weight percent. Use of the preferred color former of the invention, within the stated proportions, provides the beneficial properties of fade resistance and hue stability and, particularly, an improved resistance to CB decline. While fade and hue are related properties, a significant distinction is to be noted in that fade relates to dissipation of the color as such whereas hue stability relates to a resistance against a change in color. As noted above, CB decline is a very significant property and a most disadvantageous problem encountered in the prior art. The effect of an unsatisfactory CB decline results in a premature reduction in the ability to form an image in the pressure-sensitive record material upon light exposure of the CB coating prior to its use.

The solvent system for the chromogenic material is another important factor in the present invention. Suitable organic solvents to be employed include the following:
1. Dialkyl phthalates in which the alkyl groups thereof have from 4 to 13 carbon atoms, e.g., dibutyl phthalate, dioctylphthalate, dinonyl phthalate and ditridecyl phthalate
2. 2,2,4-trimethyl-1,3-pentanediol diisobutyrate (U.S. Pat. No. 4,027,065)
3. ethyldiphenylmethane (U.S. Pat. No. 3,996,405)
4. alkyl biphenyls such as monoisopropylbiphenyl (U.S. Pat. No. 3,627,581)
5. $C_{10}$–$C_{14}$ alkyl benzenes such as dodecyl benzene
6. diaryl ethers, di(aralkyl)ethers and aryl aralkyl ethers, ethers such as diphenyl ether, dibenzyl ether and phenyl benzyl ether
7. liquid higher dialkyl ethers (having at least 8 carbon atoms)
8. liquid higher alkyl ketones (having at least 9 carbon atoms)
9. alkyl or aralkyl benzoates, e.g., benzyl benzoate
10. alkylated naphthalenes
11. partially hydrogenated terphenyls These solvents, which are all substantially odorless, can be used alone, or in various mixtures and/or diluents. Diluents for these solvents include high-boiling straight and branched-chain hydrocarbons. The diluents are used for economic reasons but, of course, sufficient solvent must be present to dissolve the dye mixture employed. A preferred diluent is Magnaflux oil, which is a mixture of saturated aliphatic hydrocarbon oils having a distillation temperature of 320° to 550° F. Other diluents which can be employed include internal phase solvents known in the art, provided that they are not halogenated, are at least partially miscible with the solvent so as to give a single phase in the proportions used, and are not chemically reactive with the solvent or the other components of the marking liquid.

Other materials can be added to provide a beneficial effect upon the properties of the resulting marking liquid, for example, an even more substantial reduction in CB decline. Materials eligible for use in imparting CB decline resistance to marking liquids for use in pressure-sensitive record material in accordance with the invention include certain chromogenic compounds and phenol derivatives which have a free reactive position (i.e., a free ortho-or para-position). The types of materials which provide this control of CB decline can be used alone or in combination. The phenolic materials can be employed in amounts of from about 1 to about 7% by weight, preferably 2–5%, of the total marking liquid. Specific examples include dodecyl phenol; p-1,1,3,3-tetramethylbutyl phenol; 2,4-ditert-butyl phenol; p-cumylphenol; and styrenated phenol.

The capsules for the marking fluid can be prepared from gelatin as described in U.S. Pat. Nos. 2,800,457 and 3,041,289, from a urea-formaldehyde resin as disclosed in U.S. Pat. Nos. 4,001,140, 4,087,376 and 4,089,802 or from various melamine-formaldehyde resins as disclosed in U.S. Pat. No. 4,100,103.

Formulations and techniques for the preparation of the carbonless copy paper per se are well known in the art, for example, as disclosed in U.S. Pat. Nos. 3,627,581, 3,775,424 and 3,853,869. The disclosure of these patents are expressly incorporated herein by reference.

The CF sheets used with the CB sheets of the invention to form, for example, a manifold assembly of pressure-sensitive record material, are well known in the art. Substrate sheets containing oil-soluble metal salts of phenol-formaldehyde novolak resins of the type disclosed in U.S. Pat. Nos. 3,672,935; 3,732,120; and 3,737,410 are exemplary thereof. A typical preferred example of a suitable acidic resin is a zinc-modified, oil-soluble phenol-formaldehyde resin such as the zinc salt of a para-octylphenol-formaldehyde resin or the zinc salt of a para-phenylphenol-formaldehyde resin.

EXAMPLES OF THE INVENTION

The following Examples are given merely as illustrative of the present invention and are not to be considered as limiting. Unless otherwise noted, the percentages therein and throughout the application are by weight.

The various tests described in these Examples were conducted as follows:

Typewriter Intensity (TI)

The typewriter intensity (TI) test is a measure of the response of carbonless paper to a deliberate marking pressure and therefore the intensity of the resulting print. In this test a standard pattern is typed on a CF-CB (coated front-coated back) pair. The reflectance of the printed area is a measure of the color development on the CF sheet and is reported as the ratio of the reflectance of the printed area to that of the untyped area (I/Io) and is expressed as a percentage. A TI value of 100 indicates no discernible image and a lower TI value indicates a darker or more intense image.

Light Exposure (CB Decline)

Typewriter Intensity tests were also conducted before and after exposure of the CB sheet itself at the noted times to fluorescent light irradiation. The fluorescent light test device comprises a light box containing a bank of 18 daylight fluorescent lamps (21 inches long, 13 nominal lamp watts) vertically mounted on 1-inch centers placed 1½ inches from the sample being exposed.

EXAMPLES 1-16

Examples 1-16 comprise CB coatings of microcapsules of color former solutions. The capsules for Examples 1-16 were all prepared from a urea-formaldehyde polymer as disclosed in U.S. Pat. No. 4,001,140. The color former solutions were prepared for this series of examples according to the relative parts listed in Tables 1 and 2.

TABLE 1

|  | 1 | 2 | 3 | 4 | 5 | 6 | 7 | 8 |
|---|---|---|---|---|---|---|---|---|
| CVL | 3.4 | 3.4 | 3.4 | 3.4 | 3.4 | 3.4 | 3.4 | 3.4 |
| Indolyl Red | 1.1 | 1.1 | 1.1 | — | — | — | 1.2 | 1.2 |
| N-102 | 1.1 | 1.1 | 1.1 | 1.2 | 1.2 | 1.2 | 1.2 | 1.2 |
| Other color formers | — | — | — | 1.2(a) | 1.2(b) | 1.2(c) | — | — |
| Alkylate 215* | 126.4 | 126.4 | 126.4 | 130.0 | 130.0 | 130.0 | 130.0 | 130.0 |
| Ethyldiphenylmethane | 68.0 | 68.0 | 68.0 | 60.0 | 60.0 | 60.0 | 60.0 | 70.0 |
| Dodecylphenol | 10.0 | 4.0 | — | 10.0 | 10.0 | 10.0 | 10.0 | — |

*$C_{10}$–$C_{15}$ alkylbenzene
(a)spiro-7-chloro-2,6-dimethyl-3-ethylaminoxanthene-9,2-(2H)naphtho[1,8-bc]furan.
(b)3-diethylaminobenzo[b]fluoran.
(c)7-chloro-6-methyl-3-diethylamino fluoran.

TABLE 2

|  | 9 | 10 | 11 | 12 | 13 | 14 | 15 | 16 |
|---|---|---|---|---|---|---|---|---|
| Pyridyl Blue | — | 0.6 | 1.2 | 1.8 | 2.4 | — | 1.2 | 1.2 |
| CVL | 3.4 | 3.4 | 2.8 | 2.2 | 1.6 | 3.4 | 2.8 | 2.8 |
| Indolyl Red | 1.1 | 1.2 | 1.2 | 1.2 | 1.2 | 1.1 | 1.2 | 1.2 |
| N-102 | 1.1 | — | — | — | — | 1.1 | 0.6 | — |
| Alkylate 215 | 130.0 | 130.0 | 130.0 | 130.0 | 130.0 | 130.0 | 130.0 | 200.0 |
| Ethyldiphenylmethane | 70.0 | 70.0 | 70.0 | 70.0 | 70.0 | 70.0 | 70.0 | — |

For each of color former solutions 1-16, the following encapsulation procedure was used. Into a mixture of 35 parts of 10% EMA 31 (ethylene-maleic anhydride copolymer with a molecular weight range of 75,000 to 90,000, supplied by Monsanto Chemical Co.) in water, 32 parts of 20% EMA 1103 (ethylene-maleic anhydride copolymer with a molecular weight range of 5000 to 7000, supplied by Monstanto Chemical Co.) in water, 133 parts of water, 10 parts of urea and 1 parts of resorcinol, adjusted to pH 3.5, was emulsified 180 parts of the color former solution. Following emulsification, 29 parts of 37% formaldehyde was added and the mixture was placed in a 55° C. water bath with stirring. After two hours, the temperature of the water bath was allowed to equilibrate with the ambient temperature while stirring was maintained.

Each of capsule batches 1-16 was modified according to the materials and the parts listed below to prepare the respective paper coating slurries.

| Paper Coating Slurry | Parts Wet | Parts Dry |
|---|---|---|
| Capsule Slurry | 80 | 40 |
| Wheat Starch Granules | 10 | 10 |
| *Penford 230, 10% | 40 | 4 |
| Water | 100 | — |

*Etherified corn starch binder made by Penick and Ford Ltd.

The slurries were dispersed, applied to a paper base and drawn-down with a No. 12 wire-wound coating rod and the coatings dried with a heat gun. The resulting CB coatings were coupled with a sheet comprising a zinc-modified phenolic resin as disclosed in U.S. Pat. Nos. 3,732,120 and 3,737,410. The couplets were imaged in the Typewriter Intensity test previously described. The CB coatings were then exposed to light irradiation in the Fluorescent Light Exposure test previously described. The couplets were reimaged after 1 and 2 hours of the CB exposure. All TI reflectance measurements were taken at 20 minutes after imaging. The TI data obtained are presented in Table 3.

TABLE 3

| Example No. | Initial TI | Change in TI after Light Exposure of CB Coatings | |
|---|---|---|---|
| | | 1 Hr. Exposure | 2 Hr. Exposure |
| 1 | 41 | −2 | −6 |
| 2 | 43 | −3 | −7 |
| 3 | 36 | −13 | −34 |
| 4 | 41 | −6 | −15 |
| 5 | 38 | −5 | −13 |
| 6 | 38 | −8 | −15 |
| 7 | 38 | −5 | −10 |
| 8 | 35 | −18 | −32 |
| 9 | 44 | −20 | −33 |
| 10 | 41 | −17 | −29 |
| 11 | 48 | −12 | −24 |
| 12 | 41 | −12 | −20 |
| 13 | 47 | −12 | −19 |
| 14 | 35 | −15 | −31 |
| 15 | 44 | −14 | −24 |
| 16 | 46 | −14 | −24 |

The amount of decline which is acceptable is, of course, dependent upon the length of the light exposure of the CB. For a 2 hour exposure a loss (decline) of more than about 26 units is unacceptably high. Thus, Examples 1, 2, 4, 5, 6 and 7 which contained dodecylphenol and Examples 11, 12, 13, 15 and 16 which contained a sufficient amount of Pyridyl Blue produced a sufficiently low amount of CB decline to be acceptable. Examples 3, 8, 9 and 14 which were controls containing no material added to provide CB decline resistance and Example 10 which had an insufficiently low amount of Pyridyl Blue all showed an unacceptably high amount of CB decline.

EXAMPLES 17-23

The color former solutions used for Examples 17-23 all contained the following parts of the listed materials:

| | |
|---|---|
| 2.0 parts | Pyridyl Blue |
| 2.0 parts | CVL |
| 1.2 parts | Indolyl Red |
| 182.0 parts | Alkylate 215 |
| 6.0 parts | ethyldiphenylmethane |
| 6.0 parts | di-n-hexyl ketone |

In addition, each of the marking liquids contained 6.0 parts of the respective phenol listed in Table 4.

TABLE 4

| Example No. | Phenol |
|---|---|
| 17 | octyl phenol |
| 18 | dodecyl phenol |
| 19 | cumyl phenol |
| 20 | styrenated phenol |
| 21 | 4,4-methylene-bis(2-tertbutyl-6-methyl phenol) |
| 22 | 2,4,6-tri-tertbutyl phenol |
| 23 | 2,6-di-tertbutyl phenol |

The capsules for the CB coating of Examples 17-23 were all prepared from a melamine-formaldehyde resin as disclosed in U.S. Pat. No. 4,100,103. The following specific procedure was used.

Into a mixture of 35 parts of 10% EMA 31 in water and 140 parts of water, adjusted to pH 3.7, was emulsified 200 parts of the color former solution. A mixture of 32 parts of 20% EMA 1103 and 30 parts of water was adjusted to pH 4.0 and 30 parts of Resimene 714 (methylated methylol melamine resin produced by Monsanto Chemical Co.) was added thereto. This mixture was added to the emulsion and the total mixture was placed in a 55° C. water bath with stirring. After two hours, the temperature of the water bath was allowed to equilibrate with the ambient temperature while stirring was maintained.

Each of the capsule batches of Examples 17-23 was modified and coated to produce CB sheets by the same methods as used for Examples 1-16.

The resulting CB sheets were tested in the same manner as Examples 1-16. The TI data obtained are presented in Table 5.

TABLE 5

| Example No. | Initial TI | Change in TI after Light Exposure of CB Coatings | |
|---|---|---|---|
| | | 1 Hr. Exposure | 2 Hr. Exposure |
| 17 | 41 | −2 | −7 |
| 18 | 42 | −4 | −7 |
| 19 | 42 | −5 | −11 |
| 20 | 36 | −7 | −14 |
| 21 | 38 | −23 | −34 |
| 22 | 39 | −20 | −27 |
| 23 | 40 | −3 | −13 |

Using the guidelines of acceptability of less than about 26 units of decline for a 2 hour CB exposure, Examples 17, 18, 19, 20 and 23 all clearly are satisfactory. The examples which contain a phenol with no reactive group, Examples 21 and 22, clearly are unsatisfactory.

EXAMPLES 24-29

The color former solutions for Examples 24-29 were prepared according to the materials and parts listed in Table 6.

TABLE 6

| | 24 | 25 | 26 | 27 | 28 | 29 |
|---|---|---|---|---|---|---|
| Pyridyl Blue | 2.0 | 2.0 | — | 2.0 | 2.0 | 2.0 |
| CVL | 2.0 | 2.0 | 3.4 | 2.0 | 2.0 | 2.0 |
| Indolyl Red | 1.2 | 1.2 | 1.1 | 1.2 | 1.2 | 1.2 |
| N-102 | — | — | 1.1 | — | — | — |
| Other color formers | — | 1.0(d) | — | — | 1.0(e) | — |
| Alkylate 215 | 200.0 | 200.0 | 130.0 | 190.0 | 180.0 | 180.0 |
| ethyldiphenyl methane | — | — | 70.0 | — | — | — |
| dodecylphenol | — | — | — | 10.0 | — | 10.0 |
| Other additives | — | — | — | — | 20.0(f) | 10.0(g) |

(d)3,7-bis(diethylamino)-10-benzoylbenzoxazine
(e)BLMB
(f)methyl nonyl ketone
(g)methylmyristate The color former solutions of Examples 24-29 were encapsulated according to the method used for Examples 1-16. Also the capsules of Examples 24-29 were modified and coated and the resulting CB sheets tested in the same manner as used for Examples 1-16. The TI data obtained are presented in Table 7.

TABLE 7

| Example No. | Initial TI | Change in TI after Light Exposure of CB Coatins | |
|---|---|---|---|
| | | 1 Hr. Exposure | 2 Hr. Exposure |
| 24 | 43 | −8 | −13 |
| 25 | 43 | −8 | −14 |
| 26 | 39 | −13 | −34 |
| 27 | 47 | 0 | 3 |
| 28 | 39 | −5 | −11 |
| 29 | 46 | −4 | −6 |

Examples 24, 25 and 28, which contain Pyridyl Blue, all show very good CB decline resistance. Examples 27 and 29 which contain both Pyridyl Blue and dodecyl phenol show excellent CB decline resistance. Example 26 is a control containing no material added to control CB decline and is unsatisfactory.

EXAMPLES 30-32

Color former solutions for Examples 30-32 were prepared according to the materials and the parts listed in Table 8.

TABLE 8

|  | 30 | 31 | 32 |
|---|---|---|---|
| Pyridyl Blue | 91.8 | 91.8 | — |
| CVL | 21.6 | 21.6 | 91.8 |
| Indolyl Red | 27.0 | 27.0 | 14.8 |
| N-102 | 16.2 | 16.2 | 29.7 |
| 2,2,4-trimethyl-1,3-pentanediol diisobutyrate | 3495.6 | — | 3509.1 |
| Magnaflux Oil | 1747.8 | 3146.0 | 1754.6 |
| Dibutyl Phthalate | — | 2097.4 | — |

The color former solutions of Examples 30-32 were encapsulated according to a procedure similar to the method used for Examples 17-23. The following specific procedure was used to encapsulate each of the solutions.

Into a mixture of 1000 parts of 10% EMA 31 in water and 5600 parts of water, adjusted to pH 3.7, was emulsified 5400 parts of the color former solution. The pH of the emulsion was adjusted to 4.0. A mixture of 1000 parts of 10% EMA 1103 in water adjusted to pH 4.0, 1000 parts of water and 1000 parts of Resimene 714 was added to the emulsion. The resulting mixture was heated to 55° C. for 2 hours. After that time the temperature of the mixture was allowed to equilibrate with the ambient temperature while stirring was maintained.

Each of capsule batches 30-32 was modified according to the materials and the parts listed below to prepare the respective paper coating slurries.

|  | Parts Dry |
|---|---|
| Capsule Slurry | 70.40 |
| Wheat Starch Granules | 21.10 |
| Etherified Corn Starch Binder | 4.25 |
| Poly(vinyl alcohol) binder | 4.25 |

Sufficient water was incorporated to produce a 17.4% solids slurry for coating. These slurries were dispersed and coated on a paper base stock using a pilot plant air knife coater. The resulting CB coatings were tested in the same manner as Examples 1-16. The TI data obtained are presented in Table 9.

TABLE 9

| Example No. | Initial TI | Change in TI after Light Exposure of CB Coatings | |
|---|---|---|---|
|  |  | 1 Hr. Exposure | 2 Hr. Exposure |
| 30 | 46 | −2 | −9 |
| 31 | 47 | −1 | −3 |
| 32 | 53 | −17 | −30 |

Using the guideline of acceptability of less than about 26 units of decline for a 2 hour CB exposure, Examples 20 and 21, containing a sufficient amount of Pyridyl Blue, show excellent resistance to CB decline while the control with no CB decline material, Example 32, produces unsatisfactory results.

In a typical procedure the Pyridyl Blue employed in the above examples is prepared in the following manner. A quantity of 58.0 g (0.188 mole) of (1-ethyl-2-methylindol-3-yl) (3-carboxypyridin-2-yl)ketone and its isomer is stirred for 2 hours at 60°-65° C. with 35.3 g (0.188 mole) of N,N-diethyl-m-phenetidine and 250 ml of acetic anhydride. The reaction mixture is poured into 500 ml of water and the acetic anhydride hydrolyzed by slowly adding 450 ml of 29% ammonium hydroxide. After stirring for 2 hours, the resulting solid is filtered. It is washed with water, 200 ml of 40% methanol/water and 50 ml of petroleum ether (b.p. 60°-110° C.). The solid is dried in a 75° C. oven to a constant weight of 80.5 g (90%) of the desired product, Pyridyl Blue, mp 134°-137° C.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A colorless marking liquid composition having resistance to CB decline which comprises:
   (a) a colorless chromogenic color former other than Pyridyl Blue;
   (b) an organic solvent for said chromogenic color former; and
   (c) an additive for controlling CB decline selected from the group consisting of Pyridyl Blue in an amount of about 0.6 to about 1.7 parts by weight and a phenol having a free reactive position in an amount of about 2 to about 5 parts by weight, said parts by weight being based upon 100 parts by weight of total composition.

2. The colorless marking liquid of claim 1, wherein the additive for controlling CB decline is Pyridyl Blue.

3. The colorless marking liquid of claim 2, wherein the colorless chromogenic color former comprises Crystal Violet Lactone, Indolyl Red and 2'-anilino-6'-diethylamino-3'-methylfluoran.

4. The colorless marking liquid of claim 1, wherein the additive for controlling CB decline is a phenol having a free reactive position.

5. The colorless marking liquid of claim 4, wherein the phenol is dodecyl phenol.

6. The colorless marking liquid of claim 1, wherein the additive for controlling CB decline includes Pyridyl Blue and a phenol having a free reactive position.

7. The colorless marking liquid of claim 6, wherein the phenol is dodecyl phenol.

8. A pressure-sensitive record material which comprises a substrate coated with an encapsulated color-forming composition comprising:
   (a) a colorless chromogenic color former other than Pyridyl Blue;
   (b) an organic solvent for said chromogenic color former; and
   (c) an additive for controlling CB decline selected from the group consisting of Pyridyl Blue in an amount of about 0.6 to about 1.7 parts by weight and a phenol having a free reactive position in an amount of about 2 to about 5 parts by weight, said parts by weight being based upon 100 parts by weight of total composition.

9. The pressure-sensitive record of claim 8, wherein the additive for controlling CB decline in Pyridyl Blue.

10. The pressure-sensitive record material of claim 9, wherein the colorless chromogenic color former comprises Crystal Violet Lactone, Indolyl Red and 2'-anilino-6'-diethylamino-3'-methylfluoran.

11. The pressure-sensitive record material of claim 8, wherein the additive material for controlling CB decline is a phenol having a free reactive position.

12. The pressure-sensitive record material of claim 11, wherein the phenol is dodecyl phenol.

13. The pressure-sensitive record material of claim 8, wherein the additive for controlling CB decline includes Pyridyl Blue and a phenol having a free reactive position.

14. The pressure-sensitive record material of claim 13, wherein the phenol is dodecyl phenol.

* * * * *

UNITED STATES PATENT AND TRADEMARK OFFICE
CERTIFICATE OF CORRECTION

PATENT NO. : 4,275,905
DATED : June 30, 1981
INVENTOR(S) : Robert E. Miller

It is certified that error appears in the above-identified patent and that said Letters Patent are hereby corrected as shown below:

Column 10, line 60,
    after "record" insert --material--.

Column 10, line 61,
    change "in" to --is--.

Signed and Sealed this

Sixth Day of October 1981

[SEAL]

Attest:

GERALD J. MOSSINGHOFF

Attesting Officer     Commissioner of Patents and Trademarks